United States Patent
Ward et al.

(10) Patent No.: US 10,258,407 B2
(45) Date of Patent: *Apr. 16, 2019

(54) ELECTROSURGICAL GENERATOR AND SYSTEM

(71) Applicant: COVIDIEN LP, Mansfield, MA (US)

(72) Inventors: Arlen K. Ward, Englewood, CO (US); Joe D. Sartor, Longmont, CO (US); Robert H. Wham, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 295 days.

This patent is subject to a terminal disclaimer.

(21) Appl. No.: 15/267,187

(22) Filed: Sep. 16, 2016

(65) Prior Publication Data

US 2017/0000551 A1  Jan. 5, 2017

Related U.S. Application Data

(63) Continuation of application No. 14/101,495, filed on Dec. 10, 2013, now Pat. No. 9,456,862.

(Continued)

(51) Int. Cl.
*A61B 18/12* (2006.01)
*A61B 18/14* (2006.01)
*A61B 18/00* (2006.01)

(52) U.S. Cl.
CPC ...... *A61B 18/1233* (2013.01); *A61B 18/1206* (2013.01); *A61B 18/149* (2013.01);
(Continued)

(58) Field of Classification Search
CPC ............ A61B 18/1206; A61B 18/1233; A61B 18/149; A61B 2018/00607;
(Continued)

(56) References Cited

U.S. PATENT DOCUMENTS 3,923,063 A  12/1975  Andrews et al.
4,398,534 A   8/1983  Hagiwara
(Continued)

FOREIGN PATENT DOCUMENTS

DE  179607 C  3/1905
DE  390937 C  3/1924
(Continued)

OTHER PUBLICATIONS

Wald et al., "Accidental Burns", JAMA, Aug. 16, 1971, vol. 217, No. 7, pp. 916-921.

(Continued)

*Primary Examiner* — Michael F Peffley
(74) *Attorney, Agent, or Firm* — Carter, Deluca & Farrell LLP

(57) ABSTRACT

An electrosurgical generator includes an electrosurgical energy output configured to deliver electrosurgical energy to a bipolar end effector assembly in a conductive fluid environment for treating tissue. A controller having a processor is configured to control a waveform of the electrosurgical energy such that the waveform oscillates between a cut phase for initiating and sustaining tissue cutting, wherein the waveform includes a cut energy greater than the energy needed to create and sustain arcing, and a hemostasis phase, for desiccating/coagulating tissue, wherein the waveform includes a hemostasis energy less than the energy needed to sustain arcing.

16 Claims, 7 Drawing Sheets

Related U.S. Application Data

(60) Provisional application No. 61/766,470, filed on Feb. 19, 2013.

(52) U.S. Cl.
CPC ............... *A61B 2018/00607* (2013.01); *A61B 2018/00767* (2013.01); *A61B 2018/00875* (2013.01); *A61B 2018/1213* (2013.01)

(58) Field of Classification Search
CPC  A61B 2018/00767; A61B 2018/00875; A61B 2018/1213
See application file for complete search history.

(56) References Cited

U.S. PATENT DOCUMENTS

| | | | |
|---|---|---|---|
| 5,836,943 | A | 11/1998 | Miller, III |
| 5,919,191 | A | 7/1999 | Lennox et al. |
| 6,416,509 | B1 | 7/2002 | Goble et al. |
| 6,575,968 | B1 | 6/2003 | Eggers et al. |
| 6,582,427 | B1 | 6/2003 | Goble et al. |
| 6,843,789 | B2 | 1/2005 | Goble |
| 6,893,435 | B2 | 5/2005 | Goble |
| 6,966,907 | B2 | 11/2005 | Goble |
| 7,094,231 | B1 | 8/2006 | Ellman et al. |
| 7,195,627 | B2 | 3/2007 | Amoah et al. |
| 7,344,532 | B2 | 3/2008 | Goble et al. |
| D574,323 | S | 8/2008 | Waaler |
| 7,491,199 | B2 | 2/2009 | Goble |
| 2007/0038209 | A1 | 2/2007 | Buysse et al. |
| 2008/0294156 | A1 | 11/2008 | Newton et al. |
| 2009/0234349 | A1 | 9/2009 | VanDusseldorp, Sr. |
| 2009/0275938 | A1 | 11/2009 | Roggan et al. |
| 2013/0035679 | A1 | 2/2013 | Orszulak |
| 2013/0053840 | A1 | 2/2013 | Krapohl et al. |
| 2013/0066311 | A1 | 3/2013 | Smith et al. |
| 2013/0067725 | A1 | 3/2013 | Behnke, II et al. |
| 2013/0072920 | A1 | 3/2013 | Behnke, II et al. |
| 2013/0072921 | A1 | 3/2013 | Behnke, II et al. |
| 2013/0072922 | A1 | 3/2013 | Behnke, II et al. |
| 2013/0072923 | A1 | 3/2013 | Behnke, II et al. |
| 2013/0079673 | A1 | 3/2013 | Stein et al. |
| 2013/0190751 | A1 | 7/2013 | Brannan |
| 2013/0193952 | A1 | 8/2013 | Krapohl |
| 2013/0197510 | A1 | 8/2013 | Heckel |
| 2013/0197874 | A1 | 8/2013 | Heckel |
| 2013/0249721 | A1 | 9/2013 | Smith |
| 2013/0253501 | A1 | 9/2013 | Joseph |
| 2013/0261616 | A1 | 10/2013 | Prakash et al. |
| 2013/0267944 | A1 | 10/2013 | Krapohl |
| 2013/0274729 | A1 | 10/2013 | Orszulak |
| 2013/0304049 | A1 | 11/2013 | Behnke, II et al. |
| 2013/0345696 | A1 | 12/2013 | Behnke, II et al. |
| 2014/0002056 | A1 | 1/2014 | Moul et al. |
| 2014/0015535 | A1 | 1/2014 | Lopez |
| 2014/0025064 | A1 | 1/2014 | Collins |
| 2014/0163431 | A1 | 6/2014 | Orszulak et al. |

FOREIGN PATENT DOCUMENTS

| | | | |
|---|---|---|---|
| DE | 1099658 | B | 2/1961 |
| DE | 1139927 | B | 11/1962 |
| DE | 1149832 | B | 6/1963 |
| DE | 1439302 | A1 | 1/1969 |
| DE | 2439587 | A1 | 2/1975 |
| DE | 2455174 | A1 | 5/1975 |
| DE | 2407559 | A1 | 8/1975 |
| DE | 2602517 | A1 | 7/1976 |
| DE | 2504280 | A1 | 8/1976 |
| DE | 2540968 | A1 | 3/1977 |
| DE | 2820908 | A1 | 11/1978 |
| DE | 2803275 | A1 | 8/1979 |
| DE | 2823291 | A1 | 11/1979 |
| DE | 2946728 | A1 | 5/1981 |
| DE | 3143421 | A1 | 5/1982 |
| DE | 3045996 | A1 | 7/1982 |
| DE | 3120102 | A1 | 12/1982 |
| DE | 3510586 | A1 | 10/1986 |
| DE | 3604823 | A1 | 8/1987 |
| DE | 3904558 | A1 | 8/1990 |
| DE | 3942998 | A1 | 7/1991 |
| DE | 4206433 | A1 | 9/1993 |
| DE | 4339049 | A1 | 5/1995 |
| DE | 19506363 | A1 | 8/1996 |
| DE | 19717411 | A1 | 11/1998 |
| DE | 19848540 | A1 | 5/2000 |
| DE | 10 2008058737 | A1 | 4/2010 |
| EP | D 246 350 | A1 | 11/1987 |
| EP | 267403 | A2 | 5/1988 |
| EP | 296777 | A2 | 12/1988 |
| EP | 310431 | A2 | 4/1989 |
| EP | 325456 | A2 | 7/1989 |
| EP | 336742 | A2 | 10/1989 |
| EP | 390937 | A1 | 10/1990 |
| EP | 0 556 705 | A1 | 8/1993 |
| EP | 608609 | A2 | 8/1994 |
| EP | 0 836 868 | A2 | 4/1998 |
| EP | 880220 | A2 | 11/1998 |
| EP | 0 882 955 | A1 | 12/1998 |
| EP | 1051948 | A2 | 11/2000 |
| EP | 1082944 | A1 | 3/2001 |
| EP | 1366724 | A1 | 12/2003 |
| EP | 1776929 | A1 | 4/2007 |
| FR | 1 275 415 | A | 11/1961 |
| FR | 1 347 865 | A | 1/1964 |
| FR | 2 313 708 | A1 | 12/1976 |
| FR | 2364461 | A1 | 4/1978 |
| FR | 2 502 935 | A1 | 10/1982 |
| FR | 2 517 953 | A1 | 6/1983 |
| FR | 2 573 301 | A1 | 5/1986 |
| JP | 63 005876 | A | 1/1988 |
| JP | 2002-065690 | A | 3/2002 |
| JP | 2005-185657 | A | 7/2005 |
| SU | 166452 | | 1/1965 |
| SU | 727201 | A2 | 4/1980 |
| WO | 9951158 | A1 | 10/1999 |
| WO | 02/11634 | A1 | 2/2002 |
| WO | 02/45589 | A2 | 6/2002 |
| WO | 03/090635 | A1 | 11/2003 |
| WO | 2006/050888 | A1 | 5/2006 |
| WO | 2008053532 | A1 | 5/2008 |

OTHER PUBLICATIONS

Vallfors et al., "Automatically Controlled Bipolar Electrosoagulation-'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944, pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System", Innovations That Work; Company Newsletter; Sep. 1999.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

(56) References Cited

OTHER PUBLICATIONS

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.

Geddes et al., "The Measurement of Physiologic Events by Electrical Impedence", Am. J. MI, Jan. Mar. 1964, pp. 16-27.

Cosman et al., "Methods of Making Nervous System Lesions", In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance", Applied Neurophysiology 51: (1988) pp. 230-242.

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297, Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone", Neurosurgery 15: (1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300", 1 p. Sep. 1998.

Valleylab Brochure "Valleylab Electroshield Monitoring System", 2 pp. Nov. 1995.

Chinese Office Action issued in corresponding application No. 201410032725.9 dated Nov. 2, 2016.

U.S. Appl. No. 13/971,553, filed Aug. 20, 2013; inventor: Behnke.

U.S. Appl. No. 10/406,690, filed Apr. 3, 2003; inventor: Michael S. Klicek.

U.S. Appl. No. 10/573,713, filed Mar. 28, 2006; inventor: Robert H. Wham.

U.S. Appl. No. 10/761,524, filed Jan. 21, 2004; inventor: Robert Wham.

U.S. Appl. No. 11/242,458, filed Oct. 3, 2005; inventor: Daniel J. Becker.

Extended European Search Report issued in corresponding application No. 14155739.7 dated Mar. 13, 2017.

ELECTROSURGICAL GENERATOR AND SYSTEM

CROSS REFERENCE TO RELATED APPLICATIONS

The present application is a continuation application of U.S. patent application Ser. No. 14/101,495, filed on Dec. 10, 2013, now U.S. Pat. No. 9,456,862, which claims the benefit of and priority to U.S. Provisional Application Ser. No. 61/766,470, filed on Feb. 19, 2013, the entire contents of each of which are incorporated herein by reference.

BACKGROUND

Technical Field

The present disclosure relates to an electrosurgical generator and system and, more particularly, to an electrosurgical generator and system for performing surgery in a saline environment.

Background of Related Art

Transurethral resection of the prostate (TURP) is used to treat benign enlargement of the prostate, commonly referred to as benign prostatic hyperplasia (BPH). The resection includes tissue division, e.g., cutting, and hemostasis, e.g., coagulation/desiccation, of the resected tissue to control and reduce bleeding. A conventional method for treating BPH includes using a monopolar resectoscope in which current passes via an active electrode through the patient's body to a remote return electrode. Typically, a non-conductive fluid, e.g., Glycene or Sorbitol, is used for irrigating the surgical site. However, these fluids are absorbed into the body during the procedure, potentially leading to an electrolyte imbalance in the patient known as transurethral prostatic resection (TUR) syndrome. Consequently, the amount of time allowed for such surgical procedures is typically limited to one hour or less.

More recently, a TURP technique has been developed that uses a bipolar resectoscope, eliminating the need to pass current through the body to a remote return electrode and thereby reducing the risk of collateral damage caused by electrical current flowing through the patient's body. In bipolar TURP procedures, saline is used as the irrigating fluid, thus reducing the risk of the patient developing TUR syndrome. Bipolar TURP is effected at a generally slower resection pace than monopolar TURP due to the less efficient transfer of energy. However, this slower pace of resection is permissible due to the reduced risk of TUR syndrome resulting from the use of saline.

Electrosurgical generators, e.g., radiofrequency (RF) electrosurgical generators, produce waveforms that are designed to optimize cutting and hemostasis of treated tissue. However, due to the conductive properties of saline, conventional waveforms, which are configured for use in a gaseous (air) environment, have a reduced or even non-desirable effect in a conductive fluid environment, e.g., a saline environment.

SUMMARY

As used herein, the term "distal" refers to that portion that is further from an operator while the term "proximal" refers to that portion that is closer to an operator. Further, any of the aspects described herein, to the extent they are consistent, may be used in conjunction with any of the other aspects described herein.

In accordance with aspects of the present disclosure, an electrosurgical generator is provided including an electrosurgical energy output configured to deliver electrosurgical energy to a bipolar end effector assembly in a conductive fluid environment for treating tissue, and a controller. The controller includes a hardware processor configured to control a waveform of the electrosurgical energy delivered from the output to the bipolar end effector assembly such that the waveform oscillates between a cut phase and a hemostasis phase. In the cut phase, the waveform includes a cut energy $E_C$, wherein $E_C > E_{TH1}$ and $E_{TH1}$ is the energy needed to create arcing when electrosurgical energy flows between first and second electrodes of the bipolar end effector assembly via the conductive fluid. The cut phase is configured to facilitate initiating and sustaining of cutting of tissue. In the hemostasis phase, the waveform includes a hemostasis energy $E_H$, wherein $E_H < E_{TH2}$. $E_{TH2}$ is the energy needed to sustain arcing when electrosurgical energy flows between the first and second electrodes via the conductive fluid. The hemostasis phase is configured to facilitate desiccation and/or coagulation of tissue to achieve hemostasis. Optionally, the cut sustaining phase and the hemostasis phase may be separated by an effective off period to facilitate the collapse of the cutting energy field, e.g., ceasing of arcing, and vapor bubble surrounding the electrode(s). During this effective off period, power approaches zero.

In one aspect, the bipolar end effector assembly is incorporated into a bipolar resectoscope.

In another aspect, the conductive fluid is saline.

In another aspect, one or more of energies $E_C$ and $E_H$ are determined in accordance with sensed feedback data, user input, and/or empirical data.

In another aspect, one or more of energies $E_C$ and $E_H$ are determined in accordance with an impedance curve in which impedance data is correlated with energy data. Further, the impedance data may be sensed tissue impedance feedback data.

In yet another aspect, the cut phase is continued for a first time interval, and the hemostasis phase is continued for a second, different time interval. The time intervals may be controlled by the processor. More specifically, the first time interval may be between about 5 ms and about 10 ms, and the second time interval may be about 40 ms. Further, a third time interval, e.g., an effective off period wherein the power approaches zero, may be provided between the cutting phase and the hemostasis phase to collapse the arc from the cutting phase prior to application of energy in the hemostasis phase. Alternatively, this effective off period may be established through overshoot in the actual waveform produced relative to the input waveform.

In still another aspect, the first and second time intervals are determined in accordance with a movement distance of one or both of the first and second electrodes during the cut phase and the hemostasis phase, respectively.

In another aspect, the electrosurgical energy output in each of the cut and hemostasis phases is continuous.

In yet another aspect, the first and second time intervals are determined in accordance with one or more of sensed feedback data, user input, and empirical data.

In still yet another aspect, the processor receives sensed feedback data and modifies at least one of $E_C$ and $E_H$ based on the sensed feedback data. The sensed feedback data may include one or more of tissue impedance, temperature, current, voltage, power, and movement of one or both of the electrodes.

In another aspect, the waveform is a voltage waveform. In such an aspect, the cut voltage may be about 600V and the hemostasis voltage may be about 150V.

A method of treating tissue with a bipolar end effector assembly in a conductive fluid environment is also provided in accordance with aspects of the present disclosure. The method includes: applying a cut energy to initiate and sustain cutting of tissue that is greater than the energy needed to create arcing when electrosurgical energy flows between first and second electrodes of the bipolar end effector assembly via the conductive fluid; and applying a hemostasis energy to desiccate and/or coagulate tissue that is less than the arcing sustaining energy. A low power or effective off period may also be provided (or effectively established) between application of the cut energy and the hemostasis energy to allow for collapse of the arc field and the vapor bubble, similarly as described above.

In one aspect, the method includes repeatedly oscillating between the applying the cut energy and applying the hemostasis energy.

In another aspect, the method further includes receiving sensed feedback data and modifying one or more of the cut energy and the hemostasis energy based on the received feedback data.

In yet another aspect, the sensed feedback data includes tissue impedance, temperature, current, voltage, power, and/or movement of one or both of the electrodes.

In still another aspect, the method includes consulting an impedance curve in which impedance data is correlated with energy data to determine the cut voltage and the hemostasis voltage. Further, the impedance data may be sensed tissue impedance feedback data.

In still yet another aspect, the cut energy is applied for a first time interval, and the hemostasis energy is applied for a second time interval. In such an aspect, the method further includes controlling the first and second time intervals in accordance with sensed feedback data, user input, and/or empirical data.

An electrosurgical generator provided in accordance with the present disclosure includes an electrosurgical energy output configured to deliver electrosurgical energy to a bipolar end effector assembly in a conductive fluid environment for treating tissue, and a controller. The controller includes a hardware processor configured to control a waveform of the electrosurgical energy delivered from the output to the bipolar end effector assembly based on an impedance versus power curve such that the waveform oscillates between a cutting mode and a hemostasis mode.

In one aspect, a rate of power change is damped to control the waveform. More specifically, an amount of damping during power increase may be different from an amount of damping during power decrease, e.g., to differently control the waveform during the increase and decrease of power.

In accordance with further aspects of the present disclosure, an electrosurgical generator is provided including an electrosurgical energy output configured to deliver electrosurgical energy to a bipolar end effector assembly in a conductive fluid environment for treating tissue, and a controller. The controller includes a hardware processor configured to control a waveform of the electrosurgical energy delivered from the output to the bipolar end effector assembly such that the waveform oscillates between a cut initiation phase, a cut sustaining phase, and a hemostasis phase. In the cut initiation phase, the waveform includes a cut energy $E_{CI}$, wherein $E_{CI} > E_{TH1}$ and $E_{TH1}$ is the energy needed to create arcing when electrosurgical energy flows between first and second electrodes of the bipolar end effector assembly via the conductive fluid. The cut initiation phase is configured to facilitate initiation of cutting of tissue. In the cut sustaining phase, the waveform includes a cut sustaining energy $E_{CS}$, wherein $E_{TH2} < E_{CS} < E_{TH1}$, and $E_{TH2}$ is the energy needed to sustain arcing when electrosurgical energy flows between the first and second electrodes via the conductive fluid. $E_{CS}$ is less than or equal to $E_{CI}$. The cut sustaining phase is configured to facilitate, e.g., maintain, the cutting of tissue. In the hemostasis phase, the waveform includes a hemostasis energy $E_H$, wherein $E_H < E_{TH2}$. The hemostasis phase is configured to facilitate desiccation and/or coagulation of tissue to achieve hemostasis. Optionally, the cut sustaining phase and the hemostasis phase may be separated by an off period (or an effective off period) to facilitate the collapse of the cutting energy field, e.g., ceasing of arcing, and vapor bubble surrounding the electrode(s). Any of the features described above with respect to previous embodiments, or described hereinbelow, may likewise be provided.

A method of treating tissue with a bipolar end effector assembly in a conductive fluid environment is also provided in accordance with further aspects of the present disclosure. The method includes: applying a cut initiation energy to initiate cutting of tissue that is greater than the energy needed to create arcing when electrosurgical energy flows between first and second electrodes of the bipolar end effector assembly via the conductive fluid; applying a cut sustaining energy to cut tissue that is less than the create arcing energy but greater than the energy needed to sustain arcing; and applying a hemostasis energy to desiccate and/or coagulate tissue that is less than the arcing sustaining energy. A low power or off period may also be provided (or effectively established) between application of the cut sustaining energy and the hemostasis energy to allow for collapse of the arc field and the vapor bubble, similarly as described above. Any of the features described above with respect to previous embodiments, or described hereinbelow, may likewise be provided.

BRIEF DESCRIPTION OF THE DRAWINGS

Various aspects of the present disclosure are described herein with reference to the drawings wherein like reference numerals identify similar or identical elements.

DETAILED DESCRIPTION

Systems, apparatus, and methods provided in accordance with the present disclosure incorporate a generator including a controller and an electrosurgical energy output, controlled by the controller, for delivering electrosurgical energy to a bipolar end effector assembly in a conductive fluid environment to treat tissue. The controller includes a hardware processor configured to deliver continuous electrosurgical energy waveforms to the bipolar end effector assembly. This continuous electrosurgical energy waveform achieves both clinical objectives of cutting and hemostasis. More specifically, by delivering energy at or above a minimum voltage level or power sufficient to create arcs and erode tissue, cutting is achieved. On the other hand, hemostasis is achieved by delivering the voltage or power at or below a maximum level at which arcing ceases to occur. To achieve effective tissue treatment in procedures in conductive environments, e.g., in TURP procedures, relatively short bursts of higher voltage power are provided to facilitate advancement of the end effector assembly, e.g., to cut through tissue, followed by relatively longer, lower voltage periods utilized to achieve hemostasis. When transitioning from the cutting mode to the hemostasis mode, power is reduced sufficiently in order to collapse the arc field established during the cutting period. When transitioning from the hemostasis mode back to the cutting mode, power is sufficiently increased to once again initiate and sustain arcing. These and other aspects and features of the present disclosure are described in detail hereinbelow.

Figure 1:
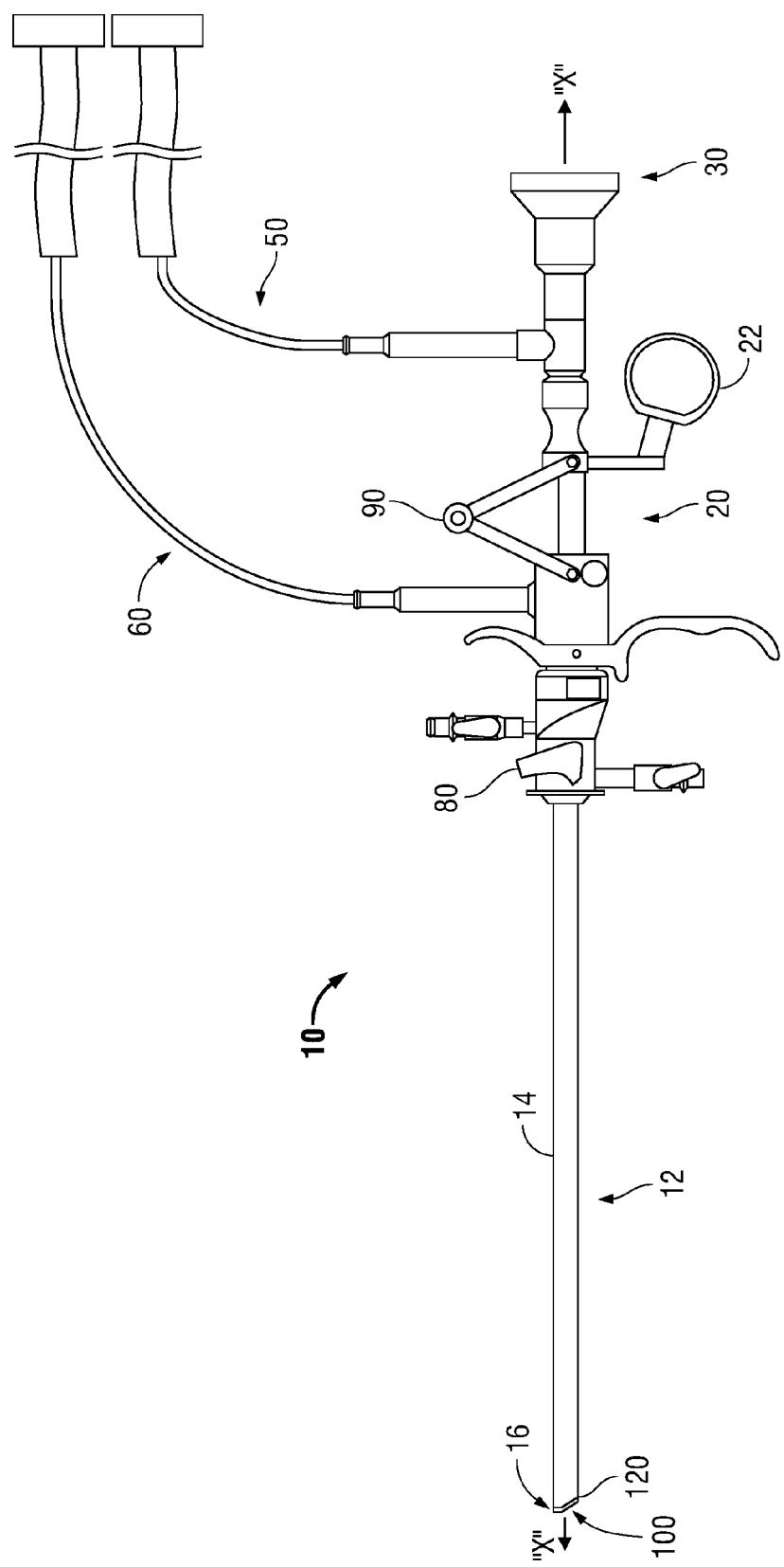
FIG. 1 is a side view of a resectoscope provided for use in accordance with the present disclosure.
Figure 2A:
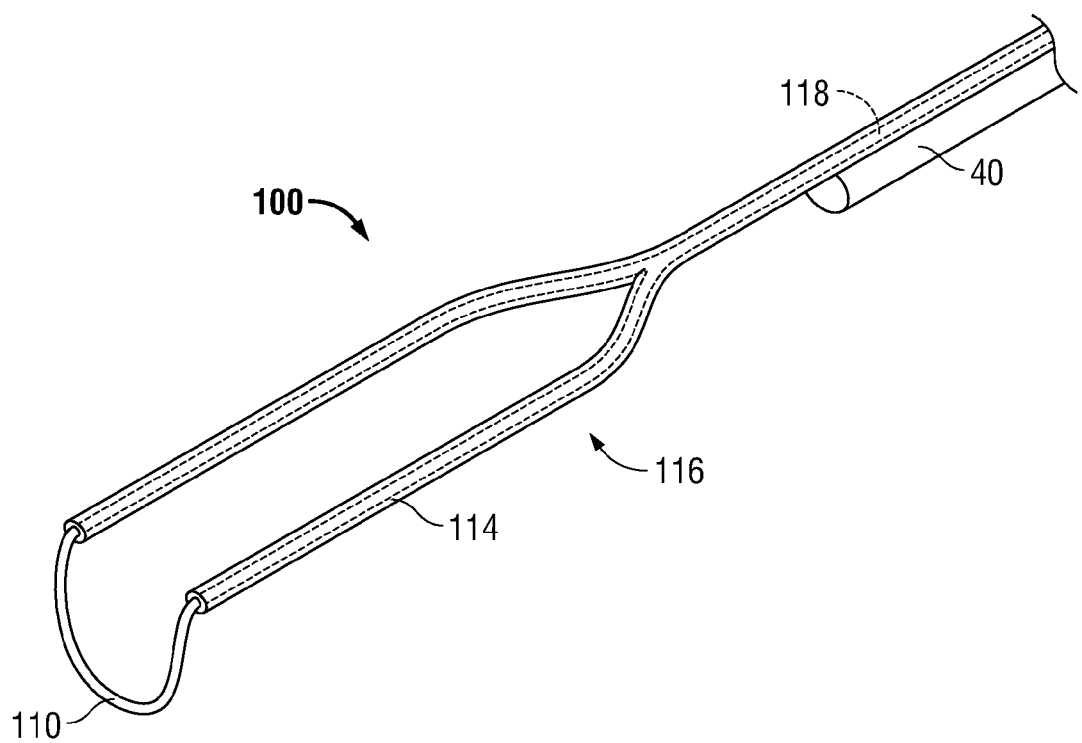
FIG. 2A is an enlarged, perspective view of an end effector assembly provided for use in accordance with the present disclosure and configured for use with the resectoscope of FIG. 1.

Turning now to FIGS. 1-2A, a bipolar electrosurgical resectoscope configured for use in accordance with the present disclosure is shown generally identified by reference numeral 10. Although resectoscope 10 is shown and described herein, it is contemplated that any suitable bipolar electrosurgical device configured to treat, e.g., ablate, cauterize, remove, cut, desiccate, coagulate, etc., tissue in a saline environment, may be provided for use in accordance with the present disclosure. For the purposes herein, resectoscope 10 is generally described.

With continued reference to FIGS. 1-2A, resectoscope 10 defines a longitudinal axis "X-X" and includes a handle assembly 20, an outer sleeve 12 extending distally from handle assembly 20, and an end effector assembly 100 operably coupled to handle assembly 20 and slidably disposed within outer sleeve 12. Handle assembly 20 is configured to facilitate the grasping of resectoscope 10 and/or the manipulation of end effector assembly 100, e.g., via actuating movable handle 22 to extend or retract end effector assembly 100 from outer sleeve 12. An endoscope 30 may be removably inserted through handle assembly 20 and outer sleeve 12 to provide the surgeon with an enhanced view of the surgical site. End effector assembly 100 may include a guide tube 40 coupled thereto to facilitate the introduction of endoscope 22 through outer sleeve 12 and into the surgical site.

Outer sleeve 12 of resectoscope 10 is formed from an electrically-conductive material that is substantially coated, or surrounded, on both its inner and outer surfaces with an insulator 14. However, distal portion 16 of outer sleeve 12 is exposed, i.e., insulator 14 does not completely extend to the distal end of outer sleeve 12, such that outer sleeve 12 defines an electrically-conductive distal portion 16. Electrically-conductive distal portion 16 of outer sleeve 12 functions as the return electrode 120 of resectoscope 10. Outer sleeve 12 further includes an exposed, electrically-conductive proximal portion (not explicitly shown) that is disposed within handle assembly 20. The exposed, electrically-conductive proximal portion (not explicitly shown) of outer sleeve 12 is configured to facilitate electrical coupling of outer sleeve 12, and, thus, return electrode 120, to an energy source, e.g., generator 200 (FIGS. 3 and 5), via second connector cable 60, as will be described in greater detail below.

Figure 3:
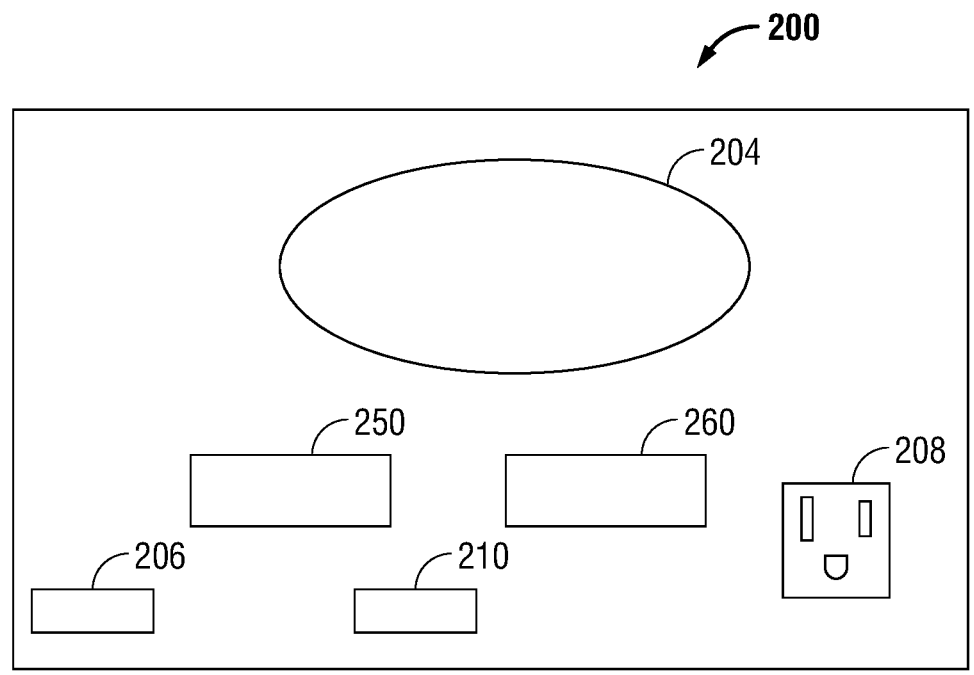
FIG. 3 is front view of a generator provided in accordance with the present disclosure and configured for use with the resectoscope of FIG. 1.
Figure 5:
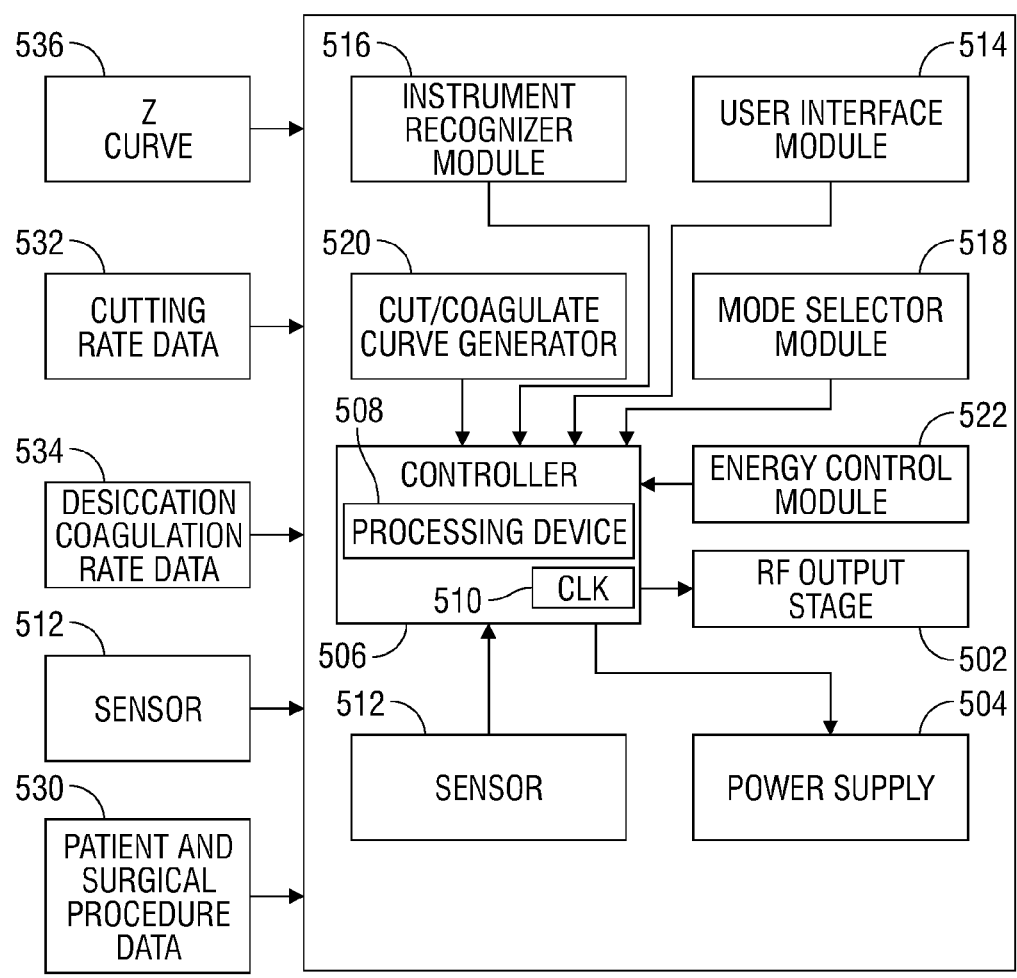
FIG. 5 is a block diagram of the generator of FIG. 3.

Resectoscope 10 may further include a position sensor 90 operably connected to the energy source, e.g., generator 200 (FIGS. 3 and 5). The generator 200 (FIGS. 3 and 5) uses the position or position derivative, i.e., velocity, to adjust the time durations of the cutting and hemostatic phases, which will be described in greater detail below. More specifically, a slower moving electrode 110 will generally require less hemostatic effect and a faster moving electrode 110 will generally require increased cutting effect. Additionally, the generator 200 (FIGS. 3 and 5) may be configured to be inactive for use in the cutting mode unless electrode 110 is being moved in the direction of cut, although the generator 200 (FIGS. 3 and 5) may be activated for use in the coagulation mode for static hemostasis. Typically, cutting is used as the electrode 110 is moved proximally from the distal extent of travel. However, direction of cutting is user selectable at the generator 200 (FIGS. 3 and 5) and may be distal to proximal, proximal to distal, or both. Alternately, sensor 90 may detect the force applied to the resectoscope 10 to move the cutting loop electrode 110 through the tissue and in similar manner adjust the durations of the cutting and hemostatic phases in order to maintain constant drag.

Referring to FIG. 2A, in conjunction with FIG. 1, end effector assembly 100 includes a wire loop electrode 110 extending from an insulative tube 114 having a Y-shaped distal portion 116. Wire loop electrode 110 functions as the active electrode 110 of resectoscope 10 while, as mentioned above, electrically-conductive distal portion 16 of outer sleeve 12 functions as the return electrode 120. More specifically, when wire loop electrode 110 is energized, current flows from wire loop electrode 110 to tissue to treat tissue. When sufficient voltage is applied to wire loop electrode 110, arcing may occur, thus facilitating the cutting of tissue. On the other hand, at lower voltages, e.g., where arcing does not occur, desiccation/coagulation of tissue may be effected to achieve hemostasis. Upon passage through tissue, energy is returned through tissue or the surrounding conductive fluid to return electrode 120 and, ultimately, back to the energy source, e.g., generator 200 (FIGS. 3 and 5). Although wire loop electrode 110 is configured for use in a conductive fluid environment, e.g., a saline environment, end effector assembly 100 may alternatively be configured for use in other surgical environments.

Referring to FIG. 2A, in conjunction with FIG. 1, an elongated portion 118 of wire loop electrode 110, which is housed within insulative tube 114, extends proximally through both insulative tube 114 and outer sleeve 12 of resectoscope 10, ultimately coupling to first connector cable 50 to facilitate electrical coupling of wire loop electrode 110 to an energy source, e.g., generator 200 (FIGS. 3 and 5). As mentioned above, return electrode 120 of outer sleeve 12 is coupled to generator 200 (FIGS. 3 and 5) via second cable connector 60. That is, electrodes 110, 120 are electrically coupled to generator 200 (FIGS. 3 and 5) via respective cable connectors 50, 60 for transmitting energy between generator 200 (FIGS. 3 and 5) and end effector assembly 100. Further, when end effector 100 is disposed in the extended position, wherein wire loop electrode 110 extends distally from outer sleeve 12, electrodes 110, 120 are positioned relative to one another to facilitate the transmission of electrosurgical energy from active electrode 110, through tissue and/or a conductive fluid, e.g., saline, to treat tissue, and the return of energy to generator 200 (FIGS. 3 and 5) via return electrode 120 of outer sleeve 12. More specifically, during treatment, an electrosurgical signal is provided from generator 200 (FIGS. 3 and 5) to energize wire loop electrode 110 while the electrodes 110, 120 are both disposed, e.g., immersed, in physical and electrical contact with tissue and/or the conductive fluid, e.g., saline, thereby creating a current path permitting current to pass from active electrode 110, through tissue and/or the saline, to return electrode 120. As electrosurgical energy is applied from active electrode 110 to tissue in contact therewith or in close proximity thereto, tissue treatment, e.g., cutting of tissue and/or desiccation/coagulation of tissue to achieve hemostasis, is effected.

As mentioned above, resectoscope 10 is configured for use in a conductive fluid environment, e.g., a saline environment. Saline may be introduced into a surgical site to distend the surgical site, provide proper conductivity, irrigate the surgical site, and/or to keep gases from entering the surgical site. Saline is commonly used because of its conductivity and isotonic properties, e.g., since saline is similar in composition to other bodily fluids. The saline may be provided to the surgical site via an irrigation system (not shown) that is integrated with resectoscope 10, or independent therefrom.

Figure 2B:
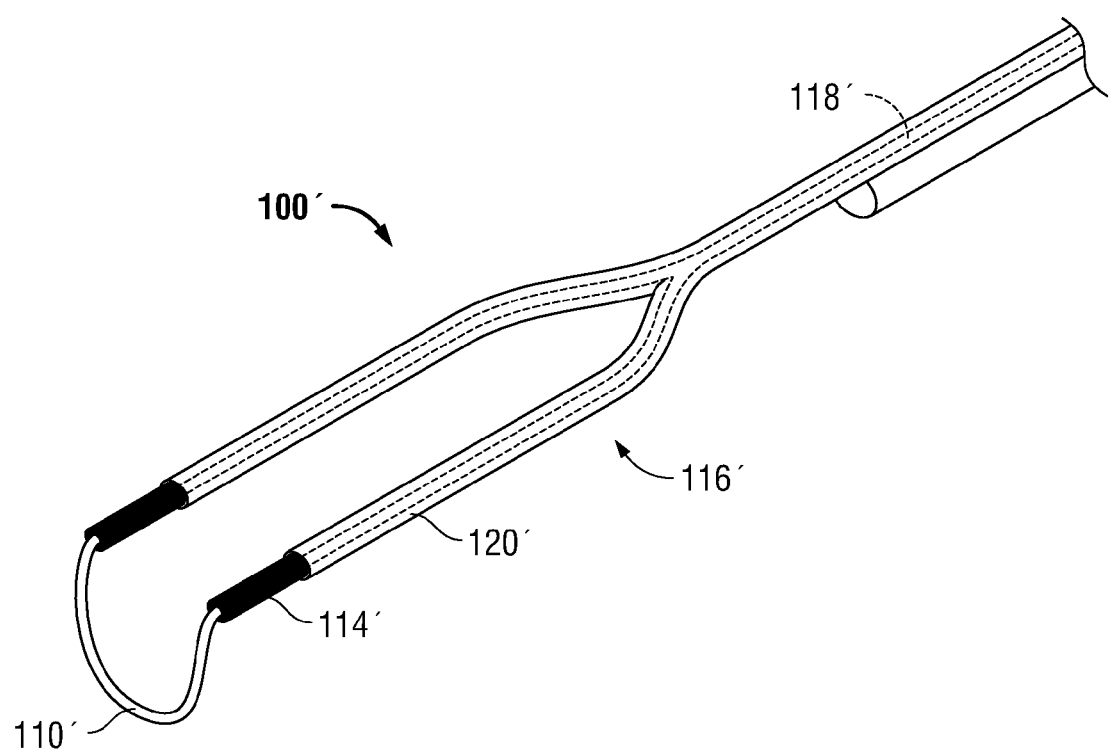
FIG. 2B is an enlarged, perspective view of another end effector assembly provided for use in accordance with the present disclosure and configured for use with a resectoscope similar to the resectoscope of FIG. 1.

Turning now to FIG. 2B, another embodiment of an end effector assembly similar to end effector assembly 100 (FIG. 2A) and configured for use with a resectoscope similar to resectoscope 10 (FIG. 1) is shown generally designated by reference numeral 100'. End effector assembly 100' includes a wire loop electrode 110' extending distally from an insulative tube 114' having a Y-shaped distal portion 116'. Insulative tube 114', in turn, extends through and distally from an outer conductive member 120' that serves as the return electrode 120' of end effector assembly 100'. In other words, end effector assembly 100' differs from end effector assembly 100 (FIG. 2A) in that an outer conductive member 120' disposed about insulative tube 114' of end effector assembly 100' functions as the return electrode 120', obviating the need to provide an electrically-conductive distal portion 16 of outer sleeve 12 (see FIG. 1). Insulative tube 114' provides sufficient separation between active and return electrodes 110', 120', respectively, to inhibit shorting. Similarly as described above with respect to end effector assembly 100 (FIG. 2A), elongated portion 118' of wire loop electrode 110' is ultimately coupled to first connector cable 50 (FIG. 1) to facilitate electrical coupling of wire loop electrode 110' to generator 200 (FIGS. 3 and 5), while the proximal end of outer conductive member 120' is ultimately coupled to second connector cable 60 (FIG. 1) for similar purposes.

Figure 4:
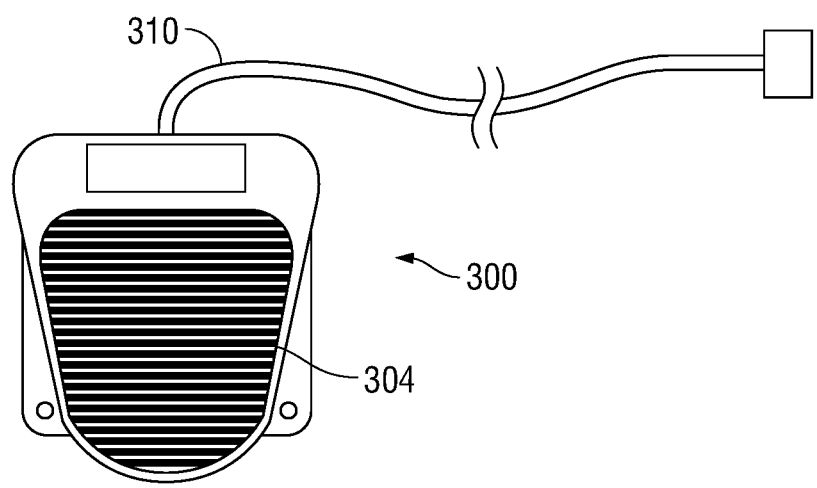
FIG. 4 is a top view of a foot pedal assembly provide for use in accordance with the present disclosure and configured for use with the generator of FIG. 3.

With reference to FIGS. 3-5, generator 200 is shown configured as a radiofrequency (RF) electrosurgical generator. Generator 200 includes an active electrode terminal 250 that is configured to receive or otherwise couple the plug-end of first cable connector 50 of resectoscope 10 (see FIG. 1) to generator 200 and a return electrode terminal 260 that is configured to receive or otherwise couple the plug-end of second cable connector 60 of resectoscope 10 (see FIG. 1) to generator 200. Generator 200 is further provided with at least one display screen 204 for displaying information to a user, an On/Off power switch 206 for activating generator 200, a power source interface 208 for coupling to a power source (not shown), and a pedal receptacle 210 for receiving the plug end of foot pedal cable connector 310 of foot pedal assembly 300. Display screen 204 may be a touch screen that allows a user to input data and/or control operation of generator 200.

As shown in FIG. 4, in conjunction with FIGS. 1-3, foot pedal assembly 300 generally includes a foot pedal 304 (multiple foot pedals 304 are also contemplated) and a foot pedal cable connector 310 configured to operably couple foot pedal 304 to generator 200 such that selective actuation of foot pedal 304 controls the application of electrosurgical energy to electrodes 110, 120 of resectoscope 10. Additionally or alternatively, one or more actuators 80 may be provided on resectoscope 10 for selectively controlling application of electrosurgical energy to electrodes 110, 120. Actuator 80 and foot pedal 304 may be configured to control the same or different functions. For example, actuator 80 and/or foot pedal 304 may be activated to select different modes of operation, e.g., a cut mode, a desiccation/coagulation mode, or a combination cut and desiccation/coagulation mode, any of which may be configured to be the default mode.

With reference to FIGS. 3 and 5, generator 200 is provided with an RF output stage 502, a power supply 504, and a controller 506 having at least one processing device 508 for controlling RF output stage 502 and/or power supply 504. Generator 200 further includes a clock (CLK) 510 for generating timing signals. One or more sensors 512 are provide for sensing and providing feedback of various parameters to controller 506. More specifically, one or more sensors 512 may be positioned at the surgical site, e.g., on resectoscope 10 (FIG. 1), and/or on or in generator 200 for measuring electrical or physical properties associated with tissue, electrodes 110, 120 of end effector assembly 100 (FIGS. 1-2A), or generator 200. Sensors 512 may be configured to measure, for example: impedance; temperature; rate of movement of electrodes 110, 120 (FIGS. 1-2A); current, voltage, and/or power (both at end effector assembly 100 (FIGS. 1-2A) and generator 200), and to relay the corresponding feedback data to controller 506.

Continuing with reference to FIGS. 3 and 5, generator 200 further includes a plurality of software modules including a user interface (UI) module 514, an instrument recognizer module 516, a mode selector module 518, a cut/coagulation curve generating module 520, and an energy control module 522. Each of these modules 514, 516, 518, 520, and 522 includes programmable instructions capable of being executed by one or more processing devices 508 and may be stored on a non-transitory computer-readable storage medium accessible by processing device 508. Suitable non-transitory computer-readable storage medium include an EEPROM, ROM, RAM, a hard drive, CD, smart card, 3.5" diskette, etc. As will be described in greater detail below, processing device 508, using modules 514, 516, 518, 520, 522 and/or other inputs, e.g., Z-curve 536, cutting rate data 532, desiccation/coagulation rate data 534, sensor data 512, patient and surgical procedure data 530, etc., controls generator 200 to perform the various functions described hereinbelow in order to achieve a desired electrosurgical effect.

UI module 514, in conjunction with processing device 508, is configured to process user input from user input devices, e.g., via the touch screen capability of display screen 204, and output information to the user, e.g., via display screen 204 and/or audible signals. Instrument recognizer module 516 recognizes when an instrument, e.g., resectoscope 10 (FIG. 1), is coupled to generator 200 by detecting the presence of cable connector 50 (FIG. 1) at active electrode terminal 250 of generator 200, and/or when an actuation device, e.g., foot pedal assembly 300, is coupled to pedal receptacle 210. Instrument recognizer module 516 may further be configured to determine the particular type of instrument and/or actuation device engaged to generator 200. When the resectoscope 10 (FIG. 1) is properly coupled to generator 200, instrument recognizer module 516 generates a "resectoscope_present" signal.

Mode selector module 518 is configured to receive user input mode selection information. For example, the user may select a treatment mode, e.g., by entering information on display screen 204. The mode of operation may alternatively or additionally be selected, as mentioned above, by actuating actuator 80 (FIG. 1) and/or foot pedal 304 (FIG. 4) to the desired mode. In either configuration, the user may select between a cutting mode, a desiccation/coagulation mode, or a combination cutting and desiccation/coagulation mode, e.g., an alternating mode that automatically transitions between cutting and desiccating/coagulating, although other modes are also contemplated. When the combination cutting and desiccation/coagulation mode is selected, mode selector module 518 generates a "cut&coagulate" signal.

Referring to FIGS. 1-2A and 5-6, once resectoscope 10 has been coupled to generator 200, e.g., once the "resectoscope_present" signal has been generated, and when resectoscope 10 is activated for use in the combination cutting and desiccating/coagulating mode, e.g., when the "cut&coagulate" signal is generated, cut/coagulation curve generator module 520 generates an energy delivery curve 600 to be followed by energy control module 522 for regulating the output of RF output stage 502 and/or power supply 504 to control the voltage provided to active electrode 110. More specifically, energy control module 522 controls the amplitude of the voltage waveform produced by RF output stage 502 and/or power supply 504 to alternate between the cutting mode and the desiccation/coagulation mode (although cut/coagulation curve generator module 520 and energy control module 522 may alternatively be configured to regulate other output energy parameters, e.g., current amplitude or power amplitude).

Energy control module 522 uses target energy characteristics (in the present example $V_1$, $V_2$, $V_3$) and/or target time limits "$t_1$," "$t_2$," "$t_3$" to control at least one of RF output stage 502 and the power supply 504, based upon the energy delivery curve 600 generated by cut/coagulation curve generator module 520. To accomplish this, energy control module 522 generates control signals for controlling one or more components of the RF output stage 502 and/or the power supply 504. Energy control module 522 may further control the RF output stage 502 and/or the power supply 504 by measuring the passage of time using CLK 510 and comparing to the time limits, e.g., "$t_1$," "$t_2$," "$t_3$."

Continuing with reference to FIGS. 1-2A and 5-6, in the cutting mode, the amplitude of the voltage waveform is increased to meet or exceed a first voltage threshold $V_{TH1}$ that corresponds to the minimum voltage necessary to create arcing between active electrode 110 and return electrode 120 when operating in a saline environment. As such, with the occurrence of arcing, tissue cutting can be readily accomplished.

Following operation in the cutting mode, cut/coagulation curve generator module 520 transitions to a desiccating/coagulating mode such that the amplitude of the voltage waveform is lowered to or below a second voltage threshold $V_{TH2}$ that corresponds to the minimum voltage necessary to sustain arcing between active electrode 110 and return electrode 120 when operating in a saline environment. In other words, once the amplitude of the voltage waveform is lowered to or below second voltage threshold $V_{TH2}$, arcing ceases to occur and, instead, desiccation/coagulation of tissue is effected to achieve hemostasis. As can be appreciated, $V_{TH1}$ is typically greater than $V_{TH2}$ since the voltage threshold necessary to create arcing is typically less than that necessary to maintain arcing.

After the desiccating/coagulating mode is complete, cut/coagulation curve generator module 520 transitions back to the cutting mode, repeating the above-described process. Cut/coagulation curve generator module 520 continuously and automatically oscillates between the cutting mode and the desiccation/coagulating mode for a pre-determined number of cycles, a predetermined amount of time, or according to start/stop input from the surgeon.

Figure 6:
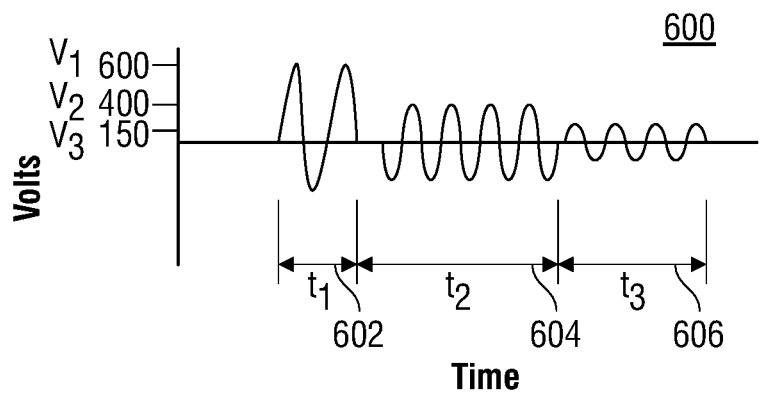
FIG. 6 is a energy delivery curve associated with an electrosurgical signal provided by the generator of FIGS. 3 and 4.

Referring to FIG. 6, in conjunction with FIG. 5, an exemplary energy delivery curve 600 is shown. The waveform represented by energy delivery curve 600 includes three phases: a first phase 602, a second phase 604, and a third phase 606. The waveform includes a target voltage amplitude $V_1$, $V_2$, $V_3$ associated with each phases 602, 604, 606, respectively. Energy delivery curve 600 may alternatively be provided in accordance with other energy characteristics and, as such, each phase 602, 604, 606 may likewise be associated with the other energy characteristic, e.g., current amplitude, power amplitude, etc.

With continued reference to FIG. 6, first phase 602 is configured to initiate cutting, e.g., to initiate operation in the cutting mode. Cutting initiation requires relatively high-voltage pulses and is continued for a first period of time "$t_1$," e.g., about 5 ms. The target voltage for first phase 602 is $V_1$, where $V_1 > V_{TH1}$. $V_1$ is indicated by way of example to be about 600V, although other voltages are contemplated. That is, first phase 602 corresponds to initiation of the cutting mode, wherein the amplitude of the voltage waveform is increased (to voltage $V_1$) to exceed first voltage threshold $V_{TH1}$, thereby heating tissue to vaporization, establishing a vapor bubble and creating arcing between active electrode 110 and return electrode 120 (see FIGS. 1-2A) in the saline environment to facilitate cutting of tissue, Second phase 604 is configured to sustain the arcing, e.g., to sustain the vaporization cutting of tissue, that was established during first phase 602. That is, second phase 604 corresponds to the (post-initiation) cutting mode. Sustaining the cutting mode requires providing relatively medium voltage pulses and is continued for a second period of time "$t_2$," e.g., about 5 ms. The amplitude of the voltage waveform for second phase 604 is $V_2$, where $V_{TH2} < V_2 < V_{TH1}$. $V_2$ is indicated by way of example to be about 400V, although other voltages are contemplated. With $V_2$ being greater than the minimum voltage required to sustain arcing, $V_{TH2}$, tissue cutting is sustained during this second phase 604. However, since arcing has already been established and since the voltage required to sustain arcing is typically less than that necessary to establish arcing, voltage $V_2$ need not be greater than $V_{TH1}$.

In some embodiments, a distinct initiation phase is not utilized. Rather, the amplitude of the voltage waveform is increased (to voltage $V_1$) and is maintained at voltage $V_1$ to both initiate and sustain the cutting mode of operation. In such configurations, the phase corresponding to the cutting mode of operation, e.g., where voltage $V_1$ is applied, may be maintained for a time period equal to $t_1+t_2$ (about 10 ms) or may be maintained for a length of time equal to $t_1$ or $t_2$ (about 5 ms). In either configuration, this results in a relatively short "burst" of high voltage power to facilitate tissue cutting while, as will be described below, in the third phase 606, which corresponds to the desiccation/coagulation mode, energy is applied at a relatively low power for a longer duration. Further, although the present disclosure is described below with respect to three phases 602, 604 606, is it contemplated that the following be equally applicable for use with two phases, simply by excluding the second phase 604 and extending the first phase 602 to include both initiating and sustaining of the cutting mode of operation.

Third phase 606 is configured to effect desiccation/coagulation of tissue to achieve hemostasis after tissue has been cut, e.g., after first and second phases 602, 604, respectively. Desiccation/coagulation requires that the electrode be in contact with tissue and that the vapor bubble associated with tissue vaporization cutting be collapsed (due to the relatively low-voltage), and is continued for a third period of time "$t_3$," e.g., about 40 ms. The amplitude of the voltage waveform for third phase 606 is $V_3$, where $V_3 < V_{TH2}$. $V_3$ is indicated by way of example to be about 150V, although other voltages are contemplated. Since $V_3$ is less than the minimum voltage required to sustain a vapor bubble and arcing in a saline environment, $V_{TH2}$, arcing does not occur and, thus, tissue cutting is substantially inhibited. Rather, at this relatively lower voltage $V_3$, contact desiccation/coagulation is effected to achieve hemostasis. In embodiments, an off-period, or low-power period may be provided between second phase 604 and third phase 606 to help ensure that arcing has ceased and the vapor bubble associated with tissue vaporization cutting is collapsed. Alternatively, as will be described below with respect to FIG. 8, overshoot in the actual waveform as compared to the input waveform may effectively establish an off-period, without the need for an actual off-period in which no energy is delivered, so as to allow for arcing to cease and the vapor bubble to collapse.

Referring to FIGS. 5-6, cut/coagulation curve generator module 520 may set or modify time intervals "$t_1$," "$t_2$," "$t_3$" and/or voltages $V_1$, $V_2$, $V_3$, according to various factors including: the first and second threshold voltages $V_{TH1}$ and $V_{TH2}$; data accessible to controller 506, e.g., patient and surgical procedure data 530 (patient age, weight, gender, body mass index (BMI), etc.), cutting rate data 532, and/or desiccation/coagulation rate data 534; the particular surgical procedure to be performed, e.g., resection of an organ, removal of a growth, etc.; the instrumentation used, e.g., resectoscope 10 (FIG. 1); and/or other considerations.

Figure 7:
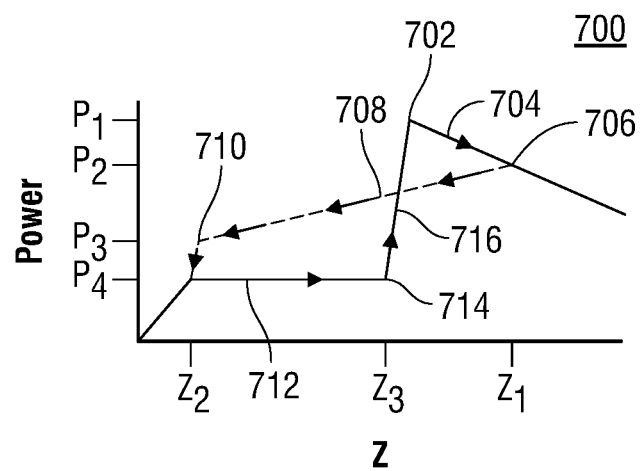
FIG. 7 is an impedance-power curve associated with electrosurgical energy applied in a conductive fluid environment.

With additional reference to FIG. 7, cut/coagulation curve generator module 520 may additionally or alternatively establish energy delivery curve 600 in accordance with an impedance curve (Z curve) 536 accessible to controller 506. Such a power versus impedance curve may be implemented, for example, such that power intentionally oscillates based on changes in tissue impedance to effect repetitive shifting between the cutting mode and the hemostasis mode. In general, when the electrode(s) is not in contact with tissue, a high impedance exists, e.g., an impedance above impedance Z3. At this point, the power is increased such that the arc initiation voltage (first phase 602, FIG. 6) is produced. When the arc is established and/or tissue is contacted by the electrode, the power is lowered such that the sustaining voltage (second phase 604, FIG. 6) is produced to sustain tissue cutting. Alternatively, as mentioned above, first phase 602 may be maintained to sustain tissue cutting without lowering the power to a sustaining level, e.g., without transitioning to a second phase 604. As the tissue is cut, creating space between the electrode and underlying fresh tissue, the impedance drops, e.g., from impedance Z1 (or an impedance above impedance Z3) to impedance Z2 (or an impedance between impedance Z2 and impedance Z3). In response, power is lowered such that the voltage drops below the arc initiation voltage, arcing is terminated, and tissue desiccation occurs, e.g., the desiccation phase (third phase 606, FIG. 6) is entered. It should be noted that during the desiccation phase, the tissue impedance may rise differently, e.g., depending on the movement rate of the electrode, and it thus may be desirable to increase or decrease the power output during this occurrence in accordance with the change in impedance. This can be implemented by varying the slope of segment 712, e.g., in a negative direction, although varying the slope in a positive direction is also contemplated. In general, it is noted that the locations and slopes of the power curve segments may vary for different electrodes and applications and that the rate at which this curve is followed is likely an important parameter. That is, the power-impedance curve 700 shown in FIG. 7 is provided for exemplary purposes only to illustrate an impedance-based implementation, and may need to be tailored according to a particular purpose.

The exemplary impedance-power curve (Z curve) 700 illustrated in FIG. 7 may be consulted for determining the energy characteristics and/or time durations of first, second, and third phases 602, 604, 606, respectively, of energy delivery curve 600 based on the impedance of tissue. That is, Z curve 700 may be used to establish the target voltage amplitudes $V_1$, $V_2$, and $V_3$ and/or time intervals "$t_1$," "$t_2$," "$t_3$" associated with phases 602, 604, 606, respectively, of energy delivery curve 600 in accordance with the impedance or change in impedance of tissue. The impedance of tissue may be measured by one or more of sensors 512 such that Z curve 700 may be dynamically implemented in response to sensed feedback information provided by the impedance sensor(s) 512, e.g., similarly as described above with respect to changing power based on changes in tissue impedance. The impedance threshold values, e.g., $Z_1$, $Z_2$, $Z_3$, may be calculated or determined based on empirical data, e.g., by accessing a look-up table storing the appropriate empirical data. Alternatively, Z curve 700 may be configured to determine other energy characteristics, e.g., current or voltage, as a function of tissue impedance. Other sensed feedback information that may be incorporated into Z curve 700 and/or energy delivery curve 600 include: temperature feedback data; current, voltage, and/or power feedback data; electrode movement feedback data, etc.

In use, during initiation of the cutting mode, e.g., during first phase 602, first power $P_1$ is supplied from generator 200 to electrodes 110, 120 (FIGS. 1-2A) to raise the amplitude of the voltage waveform above first voltage threshold $V_{TH1}$. As a result, arcing is created and tissue cutting is initiated. Point 702 of Z curve 700 corresponds to this point, the point at which cutting is initiated. During initiation, as indicated by segment 716 in FIG. 7, tissue impedance is minimally effected. Segment 716 corresponds to first phase 602, e.g., the cut-initiation phase, of the voltage waveform.

Once initiation of the cutting mode has been achieved, e.g., once first phase 602 is complete, the power supplied from generator 200 to electrodes 110, 120 (FIGS. 1-2A) is decreased at a first rate $R_1$ from first power $P_1$ to second power $P_2$ to lower the amplitude of the voltage waveform below first threshold voltage $V_{TH1}$, the voltage necessary to create arcing in a saline environment. However, although power is decreased, tissue cutting is still effected since the amplitude of the voltage waveform, at this point, is maintained above second voltage threshold $V_{TH2}$, the voltage required to maintain arcing in a saline environment. As power is decreased at first rate $R_1$ to maintain arcing to cut tissue, tissue impedance is initially increased, e.g., to impedance $Z_1$. More specifically, during tissue cutting, tissue impedance increases until tissue erodes, establishing a gap between the electrode and underlying untreated (or relatively less-treated) tissue. Upon this occurrence, impedance drops from impedance $Z_1$ since the untreated (or relatively less-treated) tissue is spaced-apart from the electrode as compared to the previously-treated tissue that has eroded. Point 706 indicates the point at which the treated tissue begins to erode to expose the further-spaced, untreated tissue. That is, point 706 indicates the point at which impedance begins to drop, corresponding to impedance $Z_1$. Upon this drop in impedance, power is decreased at a second rate $R_2$, as indicated by segment 708, from second power $P_2$ to third power $P_3$ until impedance $Z_2$ is reached at point 710. Segments 706 and 708 correspond to the second phase 604, e.g., the cutting phase, of the voltage waveform.

Alternatively, in embodiments where initiating and sustaining the cutting mode are combined into a single phase, first power $P_1$ is supplied from generator 200 to electrodes 110, 120 (FIGS. 1-2A) to raise the amplitude of the voltage waveform above first voltage threshold $V_{TH1}$. As a result, arcing is created and tissue cutting is initiated. First power $P_1$ is subsequently maintained to sustain tissue cutting. During tissue cutting, tissue impedance increases until tissue erodes, establishing a gap between the electrode and underlying untreated (or relatively less-treated) tissue. Upon this occurrence, impedance drops from impedance $Z_1$. Upon this drop in impedance, power is decreased at a second rate $R_2$, as indicated by segment 708, from second power $P_2$ to third power $P_3$ until impedance $Z_2$.

As mentioned above, and as indicated by segment 708, tissue cutting is continued during second phase 604 until impedance $Z_2$ is reached at which point, as indicated by point 710, power is decreased from third power $P_3$ to fourth power $P_4$ to drop the amplitude of the voltage waveform below second voltage threshold $V_{TH2}$, thereby stopping the occurrence of arcing and collapsing the vapor bubble. This corresponds to the third phase 606. More specifically, in third phase 606, the amplitude of the voltage waveform is dropped below the minimum voltage required to sustain arcing, $V_{TH2}$, and, thus arcing and tissue cutting cease to occur. Rather, desiccation/coagulation is effected to achieve hemostasis. During desiccation/coagulation, e.g., in the desiccation/coagulation mode, as indicated by segment 712, impedance increases as the tissue is desiccated/coagulated until it reaches impedance $Z_3$ at point 714, wherein hemostasis is achieved and/or tissue is fully desiccated/coagulated. At this point, third phase 506 is complete.

After completion of third phase 506, the power level is increased once again from fourth power $P_4$ to first power $P_1$, as indicated by segment 716, to transition from the dessicating/coagulating mode (third phase 506) to initiation of the cutting mode (first phase 502). During this increase in power, impedance does not change substantially until the power is great enough to initiate cutting, e.g., until power $P_1$ is reached. At this point, Z curve 700 has returned to point 702, wherein the above-described process is repeated to further oscillate between the two modes.

Characteristics of the Z curve 700 are provided to controller 506 via Z curve module 536, and may include: impedance values $Z_1$, $Z_2$, and $Z_3$, power values $P_1$, $P_2$, $P_3$, and $P_4$, and/or power rates $R_1$ and $R_2$. These characteristics can be selected in accordance with desired tissue effects and known tissue characteristics, e.g., via empirical data. The power levels $P_1$, $P_2$, $P_3$, and $P_4$, in turn, determine the corresponding target voltages $V_1$, $V_2$, and $V_3$ shown in FIG. 6. Further, time intervals "$t_1$," "$t_2$," and "$t_3$" may be determined by the power levels $P_1$, $P_2$, $P_3$, and $P_4$ and the power rates $R_1$, $R_2$, and/or the measured impedance values $Z_1$, $Z_2$, and $Z_3$. Additionally, the rate of power change, e.g., power rates $R_1$ and $R_2$, may be damped in order to control the amplitude and rate of oscillation of the waveform. The degree of damping may be varied depending on the power rate and/or the slope of the power rate, e.g., whether power is being increased or decreased.

With respect to TURP procedures in particular (although the following is equally applicable to other surgical procedures), since prostatic tissue is relatively soft and elastic, the surgeon often has difficulty tactically feeling short distance of movements of electrodes 110, 120 through tissue. Accordingly, the tactile response felt by the surgeon when cutting and desiccating/coagulating tends to be similar. Accordingly, the surgeon has difficulty differentiating, based on tactile feel, whether cutting or desiccation/coagulation is occurring. Thus, cutting rate data 532 and desiccation/coagulation rate data 534 may be used to provide an energy delivery curve 600 in accordance with the movement distance of electrodes 110, 120 (FIGS. 1A-2) through tissue such that tissue cutting is effected during movement of electrodes 110, 120 (FIGS. 1A-2) a first distance, followed by desiccation/coagulation of tissue during subsequent movement of electrodes 110, 120 (FIGS. 1 A-2) a second distance. That is, using rate data 532, 534, time intervals "$t_1$," "$t_2$," "$t_3$" for each phase 602, 604, 606, respectively, can be determined such that each phase corresponds to a desired movement distance of electrodes 110, 120 (FIGS. 1-2A). Initiation of the cutting mode may initially occur over an initial, relatively shorter third distance. The rate of movement of electrodes 110, 120 (FIGS. 1-2A) through tissue in each of the cutting mode and desiccation/coagulation mode may be sensed via one or more of the sensors 512, thus providing feedback in the form of cutting rate data 532 and desiccation/coagulation rate data 534. Alternatively, cutting rate data 532 and desiccation/coagulation rate data 534 may be determined empirically, calculated, or received via user input.

Figure 8:
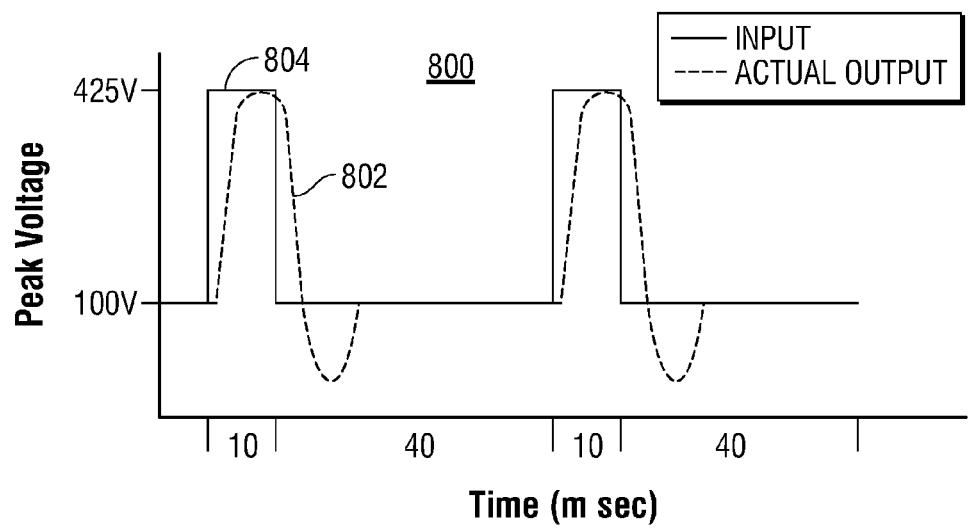
FIG. 8 is a plot of empirically-obtained waveforms associated with applying electrosurgical energy to a gel phantom.

Turning now to FIG. 8, empirical results are shown as obtained using the above-described generator 200 in accordance with the present disclosure. The input waveform 802 is a charge heuristic AC signal having a frequency of 472 kHz. The peak voltage was selected by the cut/coagulation curve generator module 520. The actual output is shown as waveform 804. In this case, the cut initiation voltage is maintained such that the cut initiation and cut sustaining phases are combined for a total duration of 10 m sec at 450V. Note the overshoot of the actual curve upon transition to the low voltage mode provides the equivalent of an off period helping to cease arcing and collapse the vapor bubble established in the cutting phases to more rapidly establish the onset of the hemostatic phase. That is, this "effective off period" may be used to facilitate transition between the cutting and hemostasis modes. The experiment results shown in FIG. 8 were obtained by performing an electrosurgical procedure on a gel phantom, cutting and coagulating at a rate of 11 mm/s. Thermal spread was measured as 5 mm.

Figure 9:
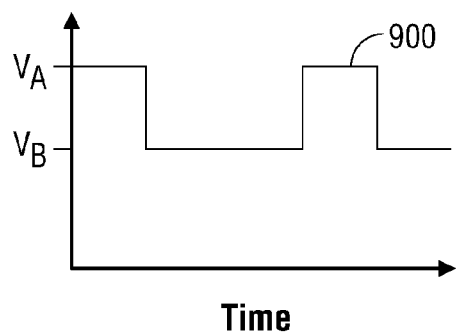
FIG. 9 is plot of an electrosurgical waveform alternating between a cutting voltage and a desiccating voltage.

Turning now to FIG. 9, another embodiment of an energy delivery curve configured to be output by generator 200 or provided to electrodes 110 in accordance with the present disclosure is shown in the form of a voltage profile of an energy delivery curve 900. Energy delivery curve 900 is similar to energy delivery curve 600 (FIG. 6) and may be implemented similarly as described above. As shown in the voltage profile of energy delivery curve 900, the characteristic voltage oscillates between a first voltage $V_A$ and second voltage $V_B$. The characteristic voltage may be, for example, the peak voltage, the peak-to-peak voltage, or the RMS voltage. Voltage $V_A$ is the cutting voltage used to initiate and sustain cutting, which is greater than $V_{TH1}$, the voltage required to create arcing in a saline environment. $V_B$ is the hemostasis voltage used to desiccate/coagulate tissue, which is below $V_{TH2}$, the voltage required to sustain an arc in a saline environment. That is, energy delivery curve 900 differs from energy delivery curve 600 (FIG. 6) in that, instead of initiating the cutting mode using a voltage $V_1$ that is above first threshold voltage $T_{TH1}$ followed by decreasing the voltage to a voltage $V_2$, that is between $V_{TH1}$ and $V_{TH2}$ (see FIG. 6), the cutting voltage $V_A$, which is greater than first threshold voltage $V_{TH1}$, is maintained throughout the cutting mode.

Figure 10:
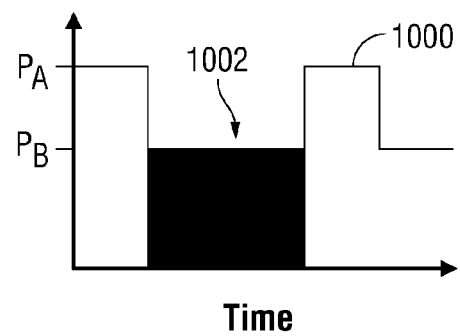
FIG. 10 is plot of an electrosurgical waveform alternating between a cutting power and a desiccating power.

With reference to FIG. 10, another energy delivery curve provided in accordance with the present disclosure is shown as a power profile of energy delivery curve 1000. The power profile of energy delivery curve 1000 includes a repeating pattern having a characteristic power that alternates between a first power $P_A$ and a second power $P_B$. The characteristic power may be, for example, the peak power, the peak-to-peak power, or the RMS power. Power $P_A$ is the cutting power used to initiate and sustain cutting, which is greater than the power required to create arcing in a saline environment. Power $P_B$ is the hemostasis power used to desiccate/coagulate tissue, which is below the power required to sustain arcing in a saline environment. That is, energy delivery curve 1000 differs from energy delivery curve 900 (FIG. 9) in that energy delivery curve 1000 is based on characteristic power, rather than characteristic voltage. With regard to energy delivery curve 1000, the shaded area 1002 below the phase of energy profile 1000 corresponds to the application of power $P_B$, wherein energy is provided in the non-arcing, non-cutting mode, e.g., the desiccation/coagulation mode. This area 1002, in turn, generally correlates to the amount of hemostasis achieved. Advantageously, the power $P_B$ and the length of time power $P_B$ is applied, e.g., the length of the desiccation/coagulation mode, can thus be selected in order to achieve a desired amount of hemostasis.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:
1. An electrosurgical generator, comprising:
an electrosurgical energy output configured to deliver electrosurgical energy to a bipolar end effector assembly; and
a controller having a hardware processor and a non-transitory computer-readable storage medium storing instructions that, when executed by the hardware processor, control a waveform of the electrosurgical energy delivered from the output to the bipolar end effector assembly such that the waveform oscillates between a first mode and a second mode, wherein the first mode is continued for a first time interval and the second mode is continued for a second time interval, and wherein the processor is configured to determine at least one of the first time interval or the second time interval in accordance with a movement distance of a portion of the bipolar end effector assembly during the at least one of the first mode or the second mode, respectively.

2. The electrosurgical generator according to claim 1, wherein the processor is configured to determine at least one of the first time interval or the second time interval in accordance with the movement distance of at least one of a first electrode or a second electrode of the bipolar end effector assembly during at least one of the first mode or the second mode.

3. The electrosurgical generator according to claim 1, wherein the first mode corresponds to a cut mode configured to facilitate cutting of tissue.

4. The electrosurgical generator according to claim 3, wherein, in the cut mode, the waveform includes a cut energy $E_C$, wherein $E_C > E_{TH1}$ and $E_{TH1}$ is the energy needed to create arcing.

5. The electrosurgical generator according to claim 1, wherein the second mode corresponds to a hemostasis mode configured to facilitate at least one of desiccation or coagulation of tissue.

6. The electrosurgical generator according to claim 5, wherein, in the hemostasis mode, the waveform includes a hemostasis energy $E_H$, wherein $E_H < E_{TH2}$ and $E_{TH2}$ is the energy needed to sustain arcing.

7. The electrosurgical generator according to claim 1, further including a third time interval between the first time interval and the second time interval, wherein during the third time interval, the waveform approaches zero.

8. The electrosurgical generator according to claim 1, wherein the processor is further configured to receive sensed feedback data and modify an energy of at least one of the first mode or the second mode based on the sensed feedback data.

9. The electrosurgical generator according to claim 1, wherein the electrosurgical energy output is configured to deliver the electrosurgical energy to the bipolar end effector assembly for use in a conductive fluid environment.

10. An electrosurgical generator, comprising:
an electrosurgical energy output configured to deliver electrosurgical energy to an electrosurgical end effector assembly; and
a controller having a hardware processor and a non-transitory computer-readable storage medium storing instructions that, when executed by the hardware processor, control a waveform of the electrosurgical energy delivered from the output to the electrosurgical end effector assembly based upon an impedance versus power curve such that the waveform oscillates between a first mode and a second mode different from the first mode.

11. The electrosurgical generator according to claim 10, wherein the electrosurgical energy output is configured to deliver the electrosurgical energy to the electrosurgical end effector assembly for use in a conductive fluid environment.

12. The electrosurgical generator according to claim 10, wherein the electrosurgical energy output is configured to deliver the electrosurgical energy to first and second electrodes of the electrosurgical end effector assembly such that the electrosurgical end effector assembly operates in a bipolar configuration.

13. The electrosurgical generator according to claim 10, wherein a rate of power change is damped.

14. The electrosurgical generator according to claim 13, wherein an amount of damping during power increase is different from an amount of damping during power decrease.

15. The electrosurgical generator according to claim 10, wherein the first mode corresponds to a cut mode configured to facilitate cutting of tissue.

16. The electrosurgical generator according to claim 10, wherein the second mode corresponds to a hemostasis mode configured to facilitate at least one of desiccation or coagulation of tissue.

* * * * *